(12) United States Patent
Cavassini et al.

(10) Patent No.: US 7,923,033 B2
(45) Date of Patent: *Apr. 12, 2011

(54) COMPOSITION OF MATTER COMPRISING PARTICLES WHICH CONTAIN CHOLINE CHLORIDE TO BE ADMINISTERED IN A RUMEN PROTECTED AND POST-RUMINALLY EFFECTIVE FORM

(75) Inventors: Paolo Cavassini, Ravenna (IT); Paolo Cicognani, Fiumana (IT); Jean Antoine Meiners, Cormondreche (CH)

(73) Assignee: Valentini S.r.L., Bertinoro (IT)

( * ) Notice: Subject to any disclaimer, the term of this patent is extended or adjusted under 35 U.S.C. 154(b) by 1222 days.

This patent is subject to a terminal disclaimer.

(21) Appl. No.: 10/802,240

(22) Filed: Mar. 17, 2004

(65) Prior Publication Data

US 2005/0019413 A1 Jan. 27, 2005

(30) Foreign Application Priority Data

Jul. 21, 2003 (IT) .............................. RN2003A0021

(51) Int. Cl.
*A61K 9/14* (2006.01)
*A61K 31/14* (2006.01)
(52) U.S. Cl. ....................................... 424/489; 514/642
(58) Field of Classification Search .................. 424/489; 514/642

See application file for complete search history.

(56) References Cited

U.S. PATENT DOCUMENTS

| 4,394,377 | A | * | 7/1983 | Spires ............................ 514/459 |
| 4,832,967 | A | | 5/1989 | Autant et al. |
| 4,948,589 | A | * | 8/1990 | Iijima et al. .................... 424/438 |
| 5,190,775 | A | | 3/1993 | Klose |
| 5,429,832 | A | | 7/1995 | Ueda et al. |
| 5,496,571 | A | | 3/1996 | Blagdon et al. |
| 5,571,527 | A | | 11/1996 | Nishimura et al. |
| 5,766,668 | A | * | 6/1998 | Brommelsiek et al. ........ 426/648 |
| 6,106,871 | A | | 8/2000 | Miller |
| 6,174,890 | B1 | * | 1/2001 | Riga et al. ...................... 514/270 |
| 6,299,912 | B1 | * | 10/2001 | Ito et al. ............................ 426/2 |
| 6,797,291 | B2 | * | 9/2004 | Richardson ........................ 426/2 |
| 2003/0129295 | A1 | | 7/2003 | Richardson |
| 2003/0148013 | A1 | | 8/2003 | Jobe |
| 2005/0064032 | A1 | | 3/2005 | Lowe et al. |
| 2006/0067984 | A1 | * | 3/2006 | Cavassini et al. .............. 424/438 |

FOREIGN PATENT DOCUMENTS

| CA | 2256256 | 6/2000 |
| EP | 0 619 079 A2 | 10/1994 |
| WO | WO 02/082921 | 10/2002 |
| WO | 03033031 A1 | 4/2003 |

OTHER PUBLICATIONS

Melting Point of Hydrogenated Soybean Oil. Accessed Jul. 22, 2008 Via http://www.parchem.com/Soybean-Oil,-hydrogenated-NF-001363.aspx.

* cited by examiner

*Primary Examiner* — Robert A Wax
*Assistant Examiner* — Aradhana Sasan
(74) *Attorney, Agent, or Firm* — Pearne & Gordon LLP

(57) ABSTRACT

A composition of matter comprising particles which contain choline chloride to be administered in a rumen-protected and post-ruminally effective form, each particle comprising a core which contains choline chloride and a protective coating surrounding the core and protecting choline chloride by ruminal activity while allowing its release into the post-rumen portion of the digestive tract of a ruminant. The core mainly consists of choline chloride in the form of a dry, crystalline powder and, in combination, the protective coating surrounding the core comprises an outer, continuous layer mainly consisting of carnauba wax and an inner, continuous layer consisting of an hydrophobic substance. A feed pellet containing the composition of matter and a premix for feed which contains the composition of matter. A premix for feed which contains feed pellets containing the composition of matter. Mash feed in unpelletted form containing the composition of matter.

51 Claims, No Drawings

COMPOSITION OF MATTER COMPRISING PARTICLES WHICH CONTAIN CHOLINE CHLORIDE TO BE ADMINISTERED IN A RUMEN PROTECTED AND POST-RUMINALLY EFFECTIVE FORM

BACKGROUND OF THE INVENTION

The present invention relates to a composition of matter comprising particles which contain choline chloride to be administered in a rumen-protected and post-ruminally effective form, in particular to a ruminant.

It has become common practice to supplement the diet of animals with certain feed additives, the use of which may either generally improve the health conditions of the animals, or increase feed efficiencies in meat producing animals, or increase milk productivity and/or milk quality in milk producing animals.

Among these additives, special attention has been recently dedicated to choline, with particular reference to the breeding of ruminants.

The term "ruminant" means an even-toed hoofed animal which has a complex of 3- or 4-chambered stomach and which is characterized by chewing again what it has already swallowed (e.g.: cattle, bison, sheep, goats and the like).

Unless otherwise stated, the term "choline" generally means choline itself, choline derivatives, a choline containing composition, a choline compound or a mixture of choline compounds. Choline is available in many forms, such as: choline, choline chloride, choline bitartrate, choline dihydrogen citrate, choline bicarbonate, choline sulphate and choline hydroxide, among other derivatives. Any choline form in principle has been considered applicable in the art, because in general choline itself, and not the form it is in, is the effective additive.

The preferred form of choline is generally choline chloride, because it is readily available and has a high specific content of choline.

Choline is an essential nutrient for normal animal growth and performance. Choline is an essential component for cell walls, nerve transmission (it is a precursor of acetyl-choline), fat metabolism and transport. Choline is also an important source of labile methyl groups (labile methyl groups which, in the diet of animals, may also be supplied by methionine and betaine and may also be synthesised using folic acid and vitamin B12).

Normally, choline is provided in adequate quantities to ruminants as a result of synthesis by ruminal microflora, e.g. in cow-feeding programs using primarily forage based diets. Protozoa appear to be the primary species involved in the synthesis of choline. Consequently, diets that result in ruminal conditions which compromise growth and proliferation of protozoa may result in inadequate choline supply to the animal and may benefit from addition of choline to the diet. Examples of these types of diets may be: high-concentrate diets, which frequently produce ruminal pH in the range of 5.5 to 5.8, which is less than optimal for proliferation of protozoa; diets providing for the inclusion of fats, which fats may induce a further reduction of the protozoan populations, probably either as a consequence of lower ruminal pH that occurs with fat feeding or as a direct effect of fats on protozoa.

Supplemental choline seems to have an effect on feed efficiencies.

Furthermore, as a lipotropic compound and a methyl donor, researchers have shown that supplemental dietary choline has an effect both on milk yield and composition. This effect has been found in ruminants and, in particular, in dairy cows.

Choline also seems to improve conveying the mobilised lipids from adipose tissues through the liver to the mammary gland.

In general choline is beneficial to the health conditions of the animals: supplemental choline may prevent "low-fat" syndrome, particularly when feeding ration of low forage: concentrate ratio.

The choline-methionine relationship appears to be critical. In periods of negative energy balance during the life of the animal, the interaction between the metabolism of methyl groups, methionine and glucose can affect methionine requirements. In the case of choline deficiencies, methionine seems to replace choline. When the methionine is at an insufficient level, the choline spares the methionine as a methyl donor. This fact suggests the possibility of supplementing choline to reduce catabolism of methionine as a methyl donor, thus probably affecting a metabolic saving of this amino acid which is essential for protein synthesis.

Incorporation of choline therefore is an important factor in supplementing the diet of ruminants. At the same time, it is recognized that choline, as many biologically active materials, when employed as a feed additive directly mixed in the ration, is inefficiently utilized by ruminants due to degradation thereof in the rumen, which is essentially a continuous fermenter. A ruminant allows a great variety of micro-organisms to live in its rumen under neutral conditions (i.e. at pHs ranging from 5 to 8) and makes advantageously use of their microbial action to digest and use ingredients (such as cellulose) which cannot inherently be digested by a mono-gastric animal and have no direct nutritive value for the host, converting them into products which can be assimilated and utilized by the host. On the other hand, the microbial action occurring in the rumen presents certain disadvantages. Very valuable substances (such as choline) may be subjected to either chemical change or digestion by the rumen micro organisms and transformed into substances of much lower nutritive value.

Therefore, choline must be supplied orally to ruminants in a rumen-protected form.

The term "ruminally protected" (or "rumen protected") means having the capability of passing through the rumen without being substantially decomposed.

It is critical that the choline be "post-ruminally effective", which means orally administered choline which passes through the rumen but does not take effect until it has reached a point past the rumen. Therefore, the rumen-protected form of choline must be capable to let choline be delivered in the abomasum and/or in its subsequent digestive tract, for efficient breeding of ruminants.

The most common technique used to produce rumen-protected choline is to encapsulate it in a protective matrix which shields choline from ruminal environment, but allows its release in the post-ruminal tract of the digestive system. The protective matrix may or may not comprise an outer, continuous coating which physically protects a core containing the active substance.

Encapsulation may be obtained by the well known fluidised-bed technology. It allows particles to be freely flowing from each other, atomising the coating material in fine droplets, which will touch the particles in movement and spread over the surface. The thin film layers of molten coating material crystallize in an air stream at a temperature lower than the melting point of the coating material. Such parameters as pressure, flow-rate and temperatures are used to optimise the process. The use of such technology is restricted to the encapsulation of compounds in solid state.

Encapsulation can furthermore be obtained by putting powdered materials to be encapsulated in a rotating device. This makes the powdered materials rotate in a helical motion along the periphery of the rotating device. At the same time a suitable binding solution is sprayed into the rotating device. The impact due to the centrifugal forces and the permanent rolling motion of the material to be encapsulated alongside the polished interior walls of the rotating device together with the binding solution produces the capsules/microcapsules.

Other technologies consist of spraying a mixture of active substance and coating material at a temperature above the melting point into an air stream at a temperature below the melting point. Spraying said mixture through a nozzle with a small opening using sufficient air-pressure will result in the formation of micro-spheres containing core and coating material. U.S. Pat. No. 5,496,571 discloses an application of this technology to the encapsulation of choline chloride, consisting of spraying a mixture of a liquid phase of choline chloride with various lipids, which results in the formation of microspheres containing liquid choline chloride and coating material. U.S. Pat. No. 5,190,775 discloses a technology for encapsulating choline chloride according to which a liquid phase of choline chloride is absorbed by a cereal carrier before applying the coating material. The so obtained granules, constituted by cereal carriers with absorbed choline chloride, may then be suspended in the coating material, which has been previously brought to the liquid state, and the suspension sprayed into a "freezing chamber". Alternatively the so obtained granules may be suspended into a flow of air and sprayed with the coating material.

Many patent documents report a number of formulations of the protective matrix which have been developed specifically for the rumen protection of numerous active substances and, in particular, for the rumen protection of choline. Given the conditions in the rumen, where the aggressive microflora lives in an aqueous environment with a pH ranging approximately from 5 to 7, most of the protective matrices developed in the art include some hydrophobic, water insoluble substance to prevent premature release of choline in the rumen, almost always mixed and combined with some hydrophilic substance to control release of choline in the post-rumen digestive tract. The protective matrices so obtained have been conceived so composed and structured as to disintegrate at acidic pH in the post ruminal tract.

As stated above, the preferred form of choline is generally choline chloride, because it is readily available and has a high specific content of choline. Choline chloride, as described above, is usually used in a liquid phase (usually in a water diluted form), either directly dispersed in the embedding matrix in the form of one or more droplets (as in U.S. Pat. No. 5,496,571), or absorbed by a cereal carrier which is, in turn, subsequently embedded in the protective matrix (as in U.S. Pat. No. 5,190,775).

In general, the extent of rumen protection offered to choline by the protective matrix may be expressed by the "rumen-by-pass quality" of the rumen protected form of choline. This "rumen-by-pass quality" (or, simply, either "rumen-by-pass" or "by-pass") may be defined as the percentage of the amount of choline originally present in the core of the capsules which is still available in the post-rumen portion of the digestive intestinal tract of the ruminant after the passage through the rumen.

Further to the fact that the compositions developed in the prior art for the protective matrix and/or for the protective coating are generally complicated and need to be provided with a very finely tuned structure and/or texture in order to be effective, the characteristic drawback of the above mentioned, existing technologies for the encapsulation or microencapsulation of choline chloride (which, as above stated, is one of the most preferred forms of supplemental choline), is that degeneration of the rumen-by-pass quality of choline chloride occurs unless the capsules are immediately administered as such to the animal, without performing any other particular operation on them. This problem is partly already recognized in the art: U.S. Pat. No. 6,106,871, in particular, clearly states that in order to prevent degradation of the choline compound prior to use, it is preferable that the rumen-protected choline compound is not mixed with any other ingredient prior to mixing with the ration and that, furthermore, it is also preferable to mix the choline compound with the ration just prior to feeding the cow.

Degeneration of the rumen-by-pass quality may occur also in either or all of the following cases: when the micro-capsules are mixed in the feed premix or in the feed mix ultimately fed to the ruminants; when, in this mixed forms, the micro-capsules are stored for a certain period of time; when the micro-capsules are subjected to a pelleting process, by which the microcapsules containing choline chloride are included in feed pellets constituting either a single ingredient of, or the whole, feed ration of the animal; when the so obtained feed pellets are stored for a given period of time prior to administering them to the ruminants.

Furthermore the nature of the coating materials usually used does not resist to the harsh conditions (mechanical pressure, thermal stresses and temperatures applied) which they are subjected to during the process of making feed pellets. Pelleting, in particular, can be defined as the agglomeration of relatively small particles into larger particles (ranging from 3 mm to 5 cm or more) by means of a mechanical process in combination with moisture, heat and pressure. The typical temperatures applied range from 55° C. to 90° C.

If the protective matrix is either not effective or damaged, so that it may show some leakages, humidity in particular becomes a concern and the damage which may be induced by humidity if the microcapsule shows some leakages (together with the consequent dramatic reduction in rumen-by-pass quality which may so result) is well known in the art. This is particularly true for choline chloride.

None of the prior art solutions is able to solve the above mentioned problems, neither deals with the problem of stability of the encapsulated choline chloride against degeneration of rumen-by-pass quality when subjected to its preparation and mixing with other feed components. All the types of micro-capsules described in the art, which contain choline chloride, are either not capable to survive to the harsh conditions of the pelleting process, or are at least insufficient to provide a good protection against a strong degeneration of rumen-by-pass quality of their choline chloride content. This may be a big problem, stated that most of cattle feed supplements in Europe and in the United States are produced in pelleted form. In this process stress caused by high temperature, pressure and/or injected steam could worsen the mechanical damage that may occur during the mixing process that is preliminarily carried out.

SUMMARY OF THE INVENTION

An object of the present invention is to provide a composition of matter comprising particles which contain choline chloride to be administered in a rumen-protected and post-ruminally effective form, which substantially reduces degeneration of rumen-by-pass-quality of choline chloride due to either a delay in the administration of this composition to the ruminant or to processes this composition may be subjected to before administration.

A further object of the present invention is to provide a composition of matter comprising particles which contain choline chloride to be administered in a rumen-protected and post-ruminally effective form, which substantially reduces the degeneration of rumen-by-pass-quality of choline chloride which is due to subjecting the composition to a process of making feed pellets in a traditional pelletization process, in particular by resisting mechanical pressures, thermal stresses and temperatures applied during a process of making feed pellets, thus increasing the post-rumen efficiency of choline chloride.

A further object of the present invention is to provide a composition of matter comprising particles which contain choline chloride to be administered in a rumen-protected and post-ruminally effective form, which substantially reduces the degeneration of rumen-by-pass-quality of choline chloride due to usual storage in atmospheric conditions present in barns and sheds commonly used to store feed, in particular under variations in temperature and/or variations in humidity, thus increasing the post-rumen efficiency of choline chloride.

A further object of the present invention is to provide a composition of matter comprising particles which contain choline chloride to be administered in a rumen-protected and post-ruminally effective form, which substantially reduces the degeneration of rumen-by-pass-quality of choline chloride due to mixing the composition with premixes (for example vitamin-mineral premixes), and/or other feed ingredient, and/or feed additives, and/or complete feed, in particular when the so mixed composition is stored for a given period of time, thus increasing the post rumen efficiency of choline chloride.

An object of the present invention is to provide a composition of matter which comprises particles containing choline chloride in such a form and so pre-treated as to further favour the micro-encapsulation process to be performed in an adequate way, such that the obtained micro-capsules/particles will better resist both the process of manufacturing of the feed pellets and of either pre-mixing in a premix or mixing in a final feed ration, as well as the storage conditions of the premix or feed ration itself, while at the same time being rumen stable and post-rumen effective.

The present invention is thus based on the encapsulation of choline chloride in its dry, crystalline form as described by the applicant in his claims. Each particle, as results from the encapsulation process, comprises a core mainly consisting of choline chloride in the form of dry crystalline powder and, in combination, a protective coating surrounding the core and comprising at least an outer, continuous layer mainly consisting of carnauba wax and an inner, continuous layer consisting of a hydrophobic substance.

Another object of the present invention is to provide feed pellets containing said composition of matter/particles.

Another object of the present invention is to provide premixes for feed containing said composition of matter/particles or containing feed pellets which in turn contain said composition of matter/particles.

Another object of the present invention is to provide a finished feed in unpelletted form, a so called "mash feed" or "Total Mixed Ration" (TMR), containing said composition of matter/particles.

These aims and others besides, which will become more apparent in the course of the description which follows, are all achieved, according to the present invention, by a composition of matter comprising particles which contain choline chloride to be administered in a rumen-protected and post-ruminally effective form (as well as by feed pellets and/or premixes for feed and/or complete feed all comprising said composition of matter/said particles) having structural and functional characteristics in accordance with the appended independent claims, further particular embodiments of the composition of matter comprising microcapsules which contain choline chloride to be administered in a rumen-protected and post-ruminally effective form (as well as of the feed pellets and/or premixes for feed and/or complete feed all comprising said composition of matter/said particles) being further individuated by the respective appended dependent claims.

The invention is illustrated in more detail in the description which follows, with the aid of the illustrative embodiments which are provided purely by way of non limiting examples.

DESCRIPTION OF THE PREFERRED EMBODIMENTS

As above mentioned, known encapsulating shells and coatings developed to provide choline chloride with rumen protection and post-rumen efficiency, even if very complicated and finely structured, do not resist both the process of manufacturing feed pellets and/or the usual mixing processes, so that degeneration of rumen-by-pass quality occurs. In particular, the applicant has been able to demonstrate that a degeneration in rumen by-pass quality is the result of a moistening of the active ingredient, in combination with a mechanical damage of the encapsulating coating protective matrix, which allows choline chloride to flow through the matrix itself and to be degraded into the ruminal fluid.

The applicant has found that a combination of a core mainly consisting of choline chloride in the form of a dry, crystalline powder with a protective coating which surrounds the core and, in turn, comprises at least an outer, continuous layer mainly consisting of carnauba wax and an inner, continuous layer consisting of a hydrophobic substance, may solve the problem, either strongly reducing or avoiding degeneration of rumen-by-pass quality, as well as giving the particles of the invention adequate resistance to the harsh mechanical and thermal conditions involved in the production of the feed pellets and/or in the mixing processes.

In detail, the composition of matter of the invention comprises particles which contain choline chloride to be administered in a rumen-protected and post-ruminally effective form. Each particle comprises a core which contains choline chloride and a protective coating surrounding the core and protecting choline chloride from ruminal activity while, at the same time, allowing its release into the post-rumen portion of a digestive tract of the ruminant.

The core mainly consists of choline chloride in the form of a dry, crystalline powder.

In combination with such a core, the protective coating surrounding the core itself comprises an outer, continuous layer mainly consisting of carnauba wax and an inner, continuous layer consisting of a hydrophobic substance.

The above mentioned structure of the particles of the invention, that is the combination of the core structure with the presence of both an inner and an outer layer composed and structured as above described, has proved to be very effective in protecting the composition of matter against degeneration of rumen-by-pass quality. As above mentioned, the feed rations contain ingredients of mineral and vegetable origin in such a particulate form that they can induce stress/rupture onto the microcapsules of the prior art during the process of (mechanical) mixing. In particular, mechanical abrasion of the surface of the microcapsule, as well as cracking due to compressive and/or shear stresses occur, which deteriorate rumen-by-pass quality almost completely. Furthermore, the pelleting operations are themselves carried out at such temperatures and pressures that damages not only of mechanical, but also of thermal origin may occur. On the contrary, the particles of the invention show a particularly relevant thermal/mechanical resistance, which the applicant has discovered to permit to overcome the mechanical and thermal stresses arising during mixing/premixing with either other feed additives or a feed ration, as well as during the pelleting process. The outer layer of the invention strongly contributes to thermal resistance. It also seems to provide very good mechanical resistance to abrasion, as well as to provide, in combination with the inner layer and the composition of the core, a strong protection of the rumen-by-pass quality even after the application of compressive and/or shear stresses like the ones occurring during either mixing or pelletting. Further improvements of this last property may be obtained by adding a predetermined, small amount of a rigidity controlling agent to the outer layer, as it will be better described in the description that follows.

As far as the core is concerned, preferably, the dry, crystalline powder of choline chloride is composed by micronized crystals having a predetermined distribution of particle size. In particular, the average particle size of the micronized crystals may range from 100 micrometers to 300 micrometers, preferably being equal to about 200 micrometers.

The core may comprise either a single crystal, or more than one crystal, or several crystals of choline chloride, depending on the size of the crystals and of the final particles.

In a preferred embodiment of the invention, the amount of dry, crystalline powder of choline chloride in the core ranges from 80% to 95% by weight of the core, and, more preferably, it ranges from 85% to 90% by weight of the core. Therefore, choline chloride in the core is in a very high concentrated form and this is an important advantage. One of the effects obtained by directly using dry crystals of choline chloride is to allow such a high concentration.

In general, the core may have a weight ranging from 30% to 70% by weight of the whole particle, and more specifically, the core may have a weight ranging from 40% to 50% by weight of the whole particle.

Advantageously, the core may comprise a predetermined amount of additional substances, in particular useful for carrying out the technological processes involved in the encapsulation and in the formation of the final particles of the invention.

The additional substances may comprise a flow modifier. The flow modifier may comprise one or more compounds chosen in the family of silicates. In particular, the flow modifier may comprise one or more compounds chosen in the group of alluminosilicates. The flow modifier may also comprise one or more compounds chosen in the group consisting of zeolites, silica, perlite. The flow modifier may be constituded either by only one of the above mentioned compounds or by any suitable combination thereof.

Furthermore, and very advantageously, in a preferred embodiment of the invention the additional substances comprise a predetermined amount of a binder acting as a moisture barrier. The dry crystals of choline chloride may thus be protected efficiently against detrimental exposures to humidity/moisture during the steps which are necessary for producing the protective coating destined to surround the core, thus avoiding the need to provide particularly dry and protected environments to carry out the handling of the choline chloride crystals and the coating process.

Preferably, the binder acting as a moisture barrier comprises one or more compounds chosen in the family of stearates. In particular, the binder acting as a moisture barrier comprises one or more compounds chosen among zinc stearate, magnesium stearate and calcium stearate. The binder may be constituded either by only one of the above mentioned compounds or by any suitable combination thereof.

Preferably, the amount of additional substances in the core ranges from 1% to 10% by weight of the core, more preferably from 2% to 8% by weight of the core. In a specific embodiment of the invention (see below) the amount of additional substances in the core is 7% by weight of the core.

As far as the protective coating is concerned, it may constitute a percentage by weight of the whole particle which ranges from 30% to 70%, preferably from 50% to 60%.

The amount of carnauba wax in the outer layer ranges from 80% to 100% by weight of the outer layer itself. Preferably, the amount of carnauba wax in the outer layer ranges from 90% to 95% by weight of the outer layer itself.

When not fully constituted by carnauba wax, as previously mentioned, advantageously the outer layer further comprises a predetermined amount of a rigidity controlling agent mixed with carnauba wax to control the rigidity of the outer layer.

The addition of the rigidity controlling agent, by partly reducing the natural rigidity of carnauba wax, may strongly improve the resistance of the outer layer against crackings due to compression and/or shear stresses which the particles may be subjected to during either the mixing or the pelleting process, thus strongly improving the resistance of the particles themselves against degeneration of rumen-by-pass quality. In order to obtain the best compromise between the need to have a very high resistance against mechanical abrasion and/or thermal stresses and the need to improve the resistance against crackings due to compression and/or shear stresses, advantageously the amount of rigidity controlling agent may be lower than or, at most equal to 20% by weight of the outer layer, but preferably it ranges from 5% to 10% by weight of the outer layer.

The rigidity controlling agent may be a plasticizer.

The rigidity controlling agent preferably comprises one or more lipids.

In particular, the one or more lipids are preferably selected from the family of vegetable oils, for example, specifically from the group consisting of palm oil and soybean oil. Preferably, at least some or all of the one or more lipids are hydrogenated vegetable oils.

The rigidity controlling agent may be constituted either by only one of the above mentioned compounds or by any suitable combination thereof.

The outer, continuous layer generally constitutes a percentage by weight of the protective coating which ranges from 30% to 60%, but preferably from 45% to 55%.

As far as the inner, continuous layer is concerned, the hydrophobic substance which constitutes it may comprise one or more lipids.

These one or more lipids are preferably selected from the family of vegetable oils. Specifically, they may be selected from the group consisting of palm oil and soybean oil. Preferably, at least some or all of the one or more lipids are hydrogenated vegetable oils.

The hydrophobic substance may also comprise stearic acid.

The hydrophobic substance may be constituted either by only one of the above mentioned compounds or by any suitable combination thereof.

The inner, continuous layer generally constitutes a percentage by weight of the protective coating which ranges from 40% to 70%, but preferably from 45% to 55%.

Various techniques for microencapsulation may be applied to produce the particles of the invention, provided they allow a dry, crystalline choline chloride powder/granule be encapsulated by the inner and outer layers of the invention.

The preferred technique is the so called fluidized bed technology.

Given the peculiar properties of the particles according to the invention, the composition of matter of the invention may be included in feed pellets by a common pelleting process with a small or negligeable reduction of its rumen-by-pass quality. In particular, according to the invention, combinations of the structure and composition of the core with the structure and composition of both the inner and the outer continuous layers may be found, which are effective to give the particles of the invention the capability to resist thermal stresses typical of the pelleting process, for example those due to temperatures ranging from 50° C. to 80° C. (or even to 90° C.).

Given the peculiar properties of the particles according to the invention, the composition of matter of the invention may be included in a premix for feed by a common premixing process with a small or negligeable reduction of its rumen-by-pass quality.

A premix is the result of a careful and efficient mixing of concentrated feed additives/ingredients in a carrier (of mineral and/or vegetable origin) in order to achieve a dilution of these concentrated ingredients into the finished feed. The use of a premix results in more efficient dosing and distribution of feed additives in the feed. The inclusion rate of a premix into the finished feed ranges from 0.5% to 20% by weight of the finished feed, typically from 1% to 7%.

In particular, according to the invention, combinations of the structure and composition of the core with the structure and composition of both the inner and the outer continuous layers may be found, which are effective to give the particles of the invention the capability to resist mixing with other feed ingredients (minerals, trace minerals, vitamins, vegetable carriers, proteic supplements, etc.) during the process of preparation of a premix.

The composition of matter of the invention may be included in the premix also by means of feed pellets previously produced, which contain the composition of matter itself.

Given the peculiar properties of the particles according to the invention, the composition of matter of the invention may be directly mixed in a mash feed in unpelletted form by a common mixing process with a small or negligeable reduction of its rumen-by-pass quality.

According to the invention, combinations of the structure and composition of the core with the structure and composition of both the inner and the outer continuous layers may be found, which are effective to give the particles of the invention the capability to be effectively stored for a predetermined interval of time in various atmospheric conditions (at temperatures ranging from −20° C. to 40° C. and/or relative humidities ranging from 20% R.H. to 80% R.H), with small or negligeable deterioration of their rumen-by-pass-quality.

According to the invention, combinations of the structure and composition of the core with the structure and composition of both the inner and the outer continuous layers may be found, which are effective to give the particles of the invention the capability to be effectively stored for a predetermined interval of time mixed in either a mash feed or in a premix (either directly or contained in feed pellets previously prepared) with a small or negligible deterioration of rumen-by-pass quality, said predetermined period of time being for example a period of time ranging from 1 to 6 months and, preferably, equal at least to 3 months.

The following examples 1-5 illustrate how to practice the invention in some of its different embodiments. They are given for illustrative purposes only and are not meant to limit the claimed invention in any manner.

EXAMPLE 1

The core contains 90% by its weight of dry crystalline choline chloride in the form of micronized crystals. The remaining 10% by weight is composed by a flow modifier (silica, 3% by weight of the core) and by a binder acting as a moisture barrier (magnesium stearate, 7% by weight of the core). The core represents 45.50% by weight of the final particle. The whole protective coating represents 54.50% by weight of the final particle. The inner, continuous layer is composed solely by hydrogenated palm oil (100% by weight of the inner layer). The outer, continuous layer is composed by carnauba wax (90% by weight of the outer layer) and by soybean oil (10% by weight of the outer layer). The inner layer represents 70% by weight of the total coating material and the 38.15% of the final particle. The outer layer represents 30% by weight of the total coating material, and 16.35% by weight of the final particle. The final particles in the composition of matter have a particle size ranging from 300 micrometers to 1200 micrometers.

EXAMPLE 2

The core contains 90% by its weight of dry crystalline choline chloride in the form of micronized crystals. The remaining 10% by weight is composed by a flow modifier (silica, 3% by weight of the core) and by a binder acting as a moisture barrier (calcium stearate, 7% by weight of the core). The core represents 39.0% by weight of the final particle. The whole protective coating represents 61.0% by weight of the final particle. The inner, continuous layer is composed solely by hydrogenated soybean oil (100% by weight of the inner layer). The outer, continuous layer is completely composed by carnauba wax (100% by weight of the outer layer). The inner layer represents 60% by weight of the total coating material and the 36.6% of the final particle. The outer layer represents 40% by weight of the total coating material, and 24.4% by weight of the final particle. The final particles in the composition of matter have a particle size ranging from 400 micrometers to 1200 micrometers.

EXAMPLE 3

The core contains 90% by its weight of dry crystalline choline chloride in the form of micronized crystals. The remaining 10% by weight is composed by a flow modifier (silica, 3% by weight of the core) and by a binder acting as a moisture barrier (calcium stearate, 7% by weight of the core). The core represents 44.2% by weight of the final particle. The whole protective coating represents 55.8% by weight of the final particle. The inner, continuous layer is composed solely by hydrogenated soybean oil (100% by weight of the inner layer). The outer, continuous layer is composed solely by carnauba wax (100% by weight of the outer layer). The inner layer represents 55% by weight of the total coating material and the 30.7% of the final particle. The outer layer represents 45% by weight of the total coating material, and 25.1% by weight of the final particle. The final particles in the composition of matter have a particle size ranging from 200 micrometers to 1000 micrometers.

EXAMPLE 4

The core contains 85% by its weight of dry crystalline choline chloride in the form of micronized crystals. The remaining 15% by weight is composed by a flow modifier (composed by perlite and silica, respectively 3% and 5% by weight of the core) and by a binder acting as a moisture barrier (calcium stearate, 7% by weight of the core). The core represents 47.2% by weight of the final particle. The whole protective coating represents 52.8% by weight of the final particle. The inner, continuous layer is composed solely by hydrogenated soybean oil (100% by weight of the inner layer). The outer, continuous layer is composed by carnauba wax (90% by weight of the outer layer) and by palm oil (10% by weight of the outer layer). The inner layer represents 55% by weight of the total coating material and the 29.0% of the final particle. The outer layer represents 45% by weight of the total coating material, and 23.8% by weight of the final particle. The final particles in the composition of matter have a particle size ranging from 400 micrometers to 1200 micrometers.

EXAMPLE 5

The core contains 85% by its weight of dry crystalline choline chloride in the form of micronized crystals. The remaining 15% by weight is composed by a flow modifier (composed by perlite and silica, respectively 3% and 5% by weight of the core) and by a binder acting as a moisture barrier (calcium stearate, 7% by weight of the core). The core represents 47.75% by weight of the final particle. The whole protective coating represents 52.25% by weight of the final particle. The inner, continuous layer is composed solely by hydrogenated soybean oil (100% by weight of the inner layer). The outer, continuous layer is composed by carnauba wax (95% by weight of the outer layer) and by palm oil (5% by weight of the outer layer). The inner layer represents 50% by weight of the total coating material and the 26.125% of the final particle. The outer layer represents 50% by weight of the total coating material, and 26.125% by weight of the final particle. The final particles in the composition of matter have a particle size ranging from 400 micrometers to 1200 micrometers.

These example formulations of the particles according to the invention have been compared with two commercially available products of the type containing liquid choline chloride absorbed by a cereal carrier (in particular: Commercial Product 1, having a choline chloride titre of 30.5% by weight of the whole product, and Commercial Product 2, having a choline chloride titre of 40.2% by weight of the whole product) as well as with three control formulations of particles containing choline chloride, specifically developed by the applicant by omitting one or more characteristic features of the invention, with the aim to make it evident that the result of the invention is reached only by the combination of its three characteristic features (a core composed by dry crystalline choline chloride, enclosed by a protective coating comprising both the inner and the outer layer as defined by the invention).

A description of the three control formulations follows.
Control 1
The core contains 85% by its weight of dry crystalline choline chloride. The remaining 15% by weight is composed by a flow modifier (zeolites, 8% by weight of the core) and by a binder acting as a moisture barrier (calcium stearate, 7% by weight of the core). The protective coating is made up by only one, continuous layer constituted only by hydrogenated palm oil (100% by weight of the protective coating). The final particles in the composition of matter have a particle size ranging from 500 micrometers to 1000 micrometers.
Control 2
The core contains 90% by its weight of dry crystalline choline chloride. The remaining 10% by weight is composed by a flow modifier (silica, 3% by weight of the core) and by a binder acting as a moisture barrier (magnesium stearate, 7% by weight of the core). The protective coating is made up by only one, continuous layer constituted only by carnauba wax (100% by weight of the protective coating). The final particles in the composition of matter have a particle size ranging from 500 micrometers to 1000 micrometers.
Control 3
The core contains 90% by its weight of dry crystalline choline chloride. The remaining 10% by weight is composed by a flow modifier (silica, 3% by weight of the core) and by a binder acting as a moisture barrier (magnesium stearate, 7% by weight of the core). The protective coating is made up by only one, continuous layer composed by a mixture of carnauba wax (50% by weight of the protective coating) and hydrogenated palm oil (50% by weight of the protective coating). The core represents 38.9% by weight of the final particle. The protective coating represents 61.1% by weight of the final particle. The final particles in the composition of matter have a particle size ranging from 300 micrometers to 800 micrometers.

Some comparative tests have been carried out, the results of which are shown in the following Tables 1-5.

Table 1 illustrates the result of a test to evaluate the degradation of rumen-by-pass quality after mixing respectively different example formulations, control formulations and commercial products of rumen protected choline chloride into a vitamin-mineral premix having the following composition:

| | |
|---|---|
| Vitamin A | 10,000,000 IU |
| Vitamin D3 | 800,000 IU |
| Vitamin E | 40,000 mg |
| Vitamin B1 | 4,000 mg |
| Vitamin B2 | 6,000 mg |
| Vitamin B6 | 2,000 mg |
| Vitamin B12 | 60 mg |
| Vitamin C | 40,000 mg |
| Vitamin K3 | 1,200 mg |
| Vitamin PP | 40,000 mg |
| Biotin | 40 mg |
| D-pantothenic acid | 4,000 mg |
| Folic acid | 2,000 mg |
| Inositol | 6,000 mg |
| Cobalt | 800 mg |
| Iodine | 2,400 mg |
| Manganese | 12,000 mg |
| Iron | 4,000 mg |
| Copper | 1,600 mg |
| Zinc | 60,000 mg |
| Selenium | 300 mg, | and having an average content of 4.5% moisture, 13.7% crude protein, 24.0% ash.
1 IU (International Unit) of vitamin A corresponds to 0.300 µg of retinol. 1 IU (International Unit) of vitamin D3 corresponds to 0.025 µg of cholecalciferol.

The particles/microcapsules containing choline chloride are in all cases included in the premix with an inclusion rate of 11% by weight of the premix.

The premix used in the test has been obtained by mixing in a stainless steel horizontal mixer of 60 litres capacity, for 15 minutes.

The titre of choline chloride can be determined: directly by non aqueous titration with perchloric acid, or indirectly through chloride determination.

By-pass has been calculated in vitro as % difference between the initial concentration and the % of choline chloride released after six hours into a buffer solution at pH=6.5 and at a temperature of 37.5° C.

Degradation of by-pass quality has been calculated as the % difference between by-pass before and after mixing.

The analysis of choline in the premix can be carried out with a spectrophotometric determination by means of an enzymatic-colorimetric method. The sample preparation is carried out by putting the premix into hot water (at a temperature of approximately 95° C.) and stirring in order to dissolve the microcapsules/particles.

Table 2 illustrates the evolution in time (during a three months period) of by-pass quality of Example 3, Example 4 and Commercial Product 1 after mixing them in the same premix used for the test illustrated in Table 1 and described above (inclusion rate of rumen protected choline chloride: 11% by weight of the premix).

Premix has been mixed in a stainless steel horizontal mixer of 60 litres capacity, for 15 minutes, and then stored in climate room at 25° C. and 65% R.H.

Table 3 illustrates the result of a test to evaluate the degradation of rumen-by-pass quality after mixing respectively different example formulations, control formulations and commercial products of rumen protected choline chloride into a proteic supplement (in particular a mixture of dry yeast and soy isolate, with a content of 5% moisture and 45% crude protein). The particles/microcapsules containing choline chloride are in all cases included in the proteic supplement with an inclusion rate of 8% by weight of the proteic supplement.

The final supplement used in the test has been obtained by mixing in a stainless steel horizontal mixer of 60 litres capacity, for 15 minutes.

The titre of choline chloride can be determined: directly by non aqueous titration with perchloric acid, or indirectly through chloride determination. By-pass has been calculated in vitro as % difference between the initial concentration and the % of choline chloride released after six hours into a buffer solution at pH=6.5 and at a temperature of 37.5° C.

Degradation of by-pass quality has been calculated as the % difference between by-pass before and after mixing.

The analysis of choline in the premix can be carried out with a spectrophotometric determination by means of an enzymatic-colorimetric method. The sample preparation is carried out by putting the supplement into hot water (at a temperature of approximately 95° C.) and stirring in order to dissolve the microcapsules/particles.

Table 4 illustrates the result of a test to evaluate the degradation of rumen-by-pass quality after mixing respectively different example formulations of rumen protected choline chloride into a mash commercial feed (composed by soybean meal, barley, ground corn, wheat bran, wheat flour, sunflower meal, soy oil, calcium carbonate, monosodium phosphate, with a content of 12% moisture, 17% crude protein, 5.3% crude fat, 4.7% crude fibre and 5.0% ash). The particles/microcapsules containing choline chloride are in all cases included in the mash commercial feed with an inclusion rate of 0.2% by weight of the mash commercial feed.

The final mash feed used in the test has been obtained by mixing for 20 minutes in a horizontal mixer at 36 rpm.

By-pass has been calculated in vitro as % difference between the initial concentration and the % of choline chloride released after six hours into a buffer solution at pH=6.5 and at a temperature of 37.5° C.

Degradation of by-pass quality has been calculated as the % difference between by-pass before and after mixing.

Table 5 illustrates the result of a test to evaluate the degradation of rumen-by-pass quality after including, by a common pelleting process, respectively different example formulations, control formulations and commercial products of rumen protected choline chloride into a pelletted feed supplement having the following composition:

| | |
|---|---|
| Full fat soy | 23.31% |
| Soybean meal | 51.27% |
| Potato meal | 6.95% |
| Vitamin-mineral premix | 6.50% |
| Ground corn | 3.84% |
| Magnesium sulphate | 2.80% |
| Calcium sulphate | 2.80% |
| Calcium carbonate | 2.54%, | and containing 11.35% moisture, 36.00% crude protein, 4.60% crude fat, 16.70% ash, 10.00% NDF, 1.94% calcium, 0.47 phosphorous, 1.23% potassium, 0.35% magnesium, 10.08% starch/sugars.

In particular, degradation of rumen-by-pass quality has been evaluated during a period of three weeks.

By-pass has been calculated in vitro as % difference between the initial concentration and the % of choline chloride released after six hours into a buffer solution at pH=6.5 and at a temperature of 37.5° C.

The analysis of choline in the pelleted feed can be carried out with a spectrophotometric determination by means of an enzymatic-colorimetric method. The sample preparation is carried out by grinding the pellet and putting the obtained product into hot water (at a temperature of approximately 95° C.) and stirring in order to dissolve the microcapsules/particles.

The invention thus conceived can be subjected to numerous modifications and variations, without thereby departing from the scope of the inventive concept that characterizes it. Moreover, all components may be replaced by other technically equivalent elements.

Numerous characteristics and advantages of the invention have been set in the foregoing description, together with details of the structure and function of the invention. The disclosure, however, is illustrative only and changes may be made in detail, within the principle of the invention, to the full extent indicated by the broad general meaning of the terms in which the appended claims are expressed.

Tables 1-5 are reported in the following pages of the description.

TABLE 1

| Product | Choline chloride titre (%) | By-pass before mixing | By-pass 24 hours after mixing | Degradation of by-pass quality |
|---|---|---|---|---|
| Example 1 | 40.6 | 85.0% | 82.8% | 2.59% |
| Example 2 | 35.2 | 65.5% | 60.3% | 7.94% |
| Example 3 | 39.8 | 85.9% | 80.7% | 6.05% |
| Example 4 | 40.1 | 89.2% | 85.6% | 4.03% |
| Commercial Product 1 | 30.5 | 82.4% | 40.6% | 50.73% |

TABLE 1-continued

| Product | Choline chloride titre (%) | By-pass before mixing | By-pass 24 hours after mixing | Degradation of by-pass quality |
|---|---|---|---|---|
| Commercial Product 2 | 40.2 | 20.3% | 4.8% | 76.36% |
| Control 1 | 42.0 | 20.6% | 5.1% | 75.24% |
| Control 2 | 39.5 | 30.3% | 12.3% | 59.41% |
| Control 3 | 35.0 | 60.5% | 45.8% | 24.30% |

TABLE 2

| Product | Choline chloride titre (%) | By pass | | | | | | |
|---|---|---|---|---|---|---|---|---|
| | | Before mixing | 7 days after mixing | 14 days after mixing | 21 days after mixing | 30 days after mixing | 60 days after mixing | 90 days after mixing |
| Ex. 3 | 39.8 | 85.9% | 79.4% | 78.2% | 77.8% | 77.1% | 75.7% | 70.3% |
| Ex. 4 | 40.1 | 89.2% | 84.3% | 82.9% | 82.5% | 82.2% | 79.5% | 75.5% |
| Comm. Prod. 1 | 30.5 | 82.4% | 13.8% | 10.7% | 5.2% | 0% | 0% | 0% |

(Ex. 3 = Example 3; Ex. 4 = Example 4; Comm. Prod. 1 = Commercial Product 1)

TABLE 3

| Products | Choline chloride titre % | By-pass before mixing | By-pass 24 hours after mixing | Degradation of by-pass quality |
|---|---|---|---|---|
| Example 1 | 40.6 | 85.0% | 82.5% | 2.59% |
| Control 1 | 42.0 | 20.6% | 2.8% | 99.42% |
| Control 2 | 39.5 | 30.3% | 11.7% | 61.39% |
| Control 3 | 35.0 | 60.5% | 44.8% | 25.30% |
| Commercial Product 1 | 30.5 | 82.4% | 30.6% | 62.86% |
| Commercial Product 2 | 40.2 | 20.3% | 2.8% | 86.20% |

TABLE 4

| Products | By-pass before mixing in the mash feed | By-pass 24 hours after mixing | Degradation of by-pass quality |
|---|---|---|---|
| Example 1 | 85.0% | 79.6% | 6.35% |
| Example 3 | 87.9% | 85.7% | 2.50% |
| Example 4 | 91.0% | 88.6% | 2.63% |

TABLE 5

| Product | Choline chloride titre % | By-pass before pelleting | Degradation of by-pass quality 1 day after pelleting | Degradation of bypass quality 21 days after pelleting |
|---|---|---|---|---|
| Example 4 | 40.1 | 81.9% | 13.9% | 20.4% |
| Example 5 | 40.6 | 86.7% | 7.7% | 18.2% |
| Control 2 | 39.5 | 28.7% | 79.8% | 97.5% |
| Control 3 | 35.0 | 56.8% | 29.0% | 35.8% |
| Commercial Product 1 | 30.5 | 40.6% | 96.3% | 100% |

What is claimed is:

1. A particle for animal feed for a ruminant, said particle comprising a core, a first layer surrounding the core, and a second layer surrounding the first layer and distinct from said first layer, said core comprising choline chloride in the form of a dry, crystalline powder and a binder, the layers together being effective to protect the choline chloride from ruminal activity while allowing effective release of the choline chloride into the post-rumen portion of the digestive tract of the ruminant, the first layer consisting essentially of a hydrophobic substance selected from the group consisting of vegetable oils, hydrogenated vegetable oils, stearic acid and mixtures thereof, said first layer providing effective protection of the choline chloride from moisture, the second layer consisting essentially of carnauba wax, said second layer being effective to protect the core and the first layer from degradation from abrasion, pressure and mechanical and thermal stress encountered during mixing and pelletization of said particles into an animal feed pellet.

2. The particle of claim 1, wherein the dry, crystalline powder of choline chloride is composed of micronized crystals having a predetermined distribution of particle size.

3. The particle of claim 2, wherein the average particle size of the micronized crystals ranges from 100 micrometers to 300 micrometers.

4. The particle of claim 2, wherein the average particle size of the micronized crystals is 200 micrometers.

5. The particle of claim 1, wherein the amount of dry, crystalline powder of choline chloride in the core ranges from 80% to 95% by weight of the core.

6. The particle of claim 1, wherein the amount of dry, crystalline powder of choline chloride in the core ranges from 85% to 90% by weight of the core.

7. The particle of claim 1, wherein the core further comprises a predetermined amount of a flow modifier.

8. The particle of claim 7, wherein the flow modifier comprises one or more compounds selected from the family of silicates.

9. The particle of claim 8, wherein the flow modifier comprises one or more compounds selected from the group of alluminosilicates.

10. The particle of claim 7, wherein the flow modifier comprises one or more compounds selected from the group consisting of zeolites, silica, and perlite.

11. The particle of claim 7, wherein the amount of flow modifier in the core ranges from 3% to 8% by weight of the core.

12. The particle of claim 7, wherein the amount of flow modifier in the core is equal to 3% by weight of the core.

13. The particle of claim 7, wherein the amount of flow modifier in the core is equal to 8% by weight of the core.

14. The particle of claim 1, wherein the binder acts as a moisture barrier.

15. The particle of claim 14, wherein the binder comprises one or more compounds selected from the family of stearates.

16. The particle of claim 15, wherein the binder comprises one or more compounds selected from zinc stearate, magnesium stearate and calcium stearate.

17. The particle of claim 1, wherein the amount of binder in the core is equal to 7% by weight of the core.

18. The particle of claim 1, wherein: the core contains 90% by its weight of dry crystalline choline chloride in the form of micronized crystals, the remaining 10% by weight of the core being composed of a flow modifier consisting of silica in an amount of 3% by weight of the core and by the binder acting as a moisture barrier consisting of calcium stearate in an amount of 7% by weight of the core; the core representing 39.0% by weight of the final particle; the first and second layers together representing 61.0% by weight of the final particle; the first layer is composed solely by hydrogenated soybean oil as hydrophobic substance; the second layer is completely composed by carnauba wax; the first layer represents 60% by weight of the two layers and 36.6% by weight of the final particle; the second layer represents 40% by weight of the two layers, and 24.4% by weight of the final particle; the final particle having a particle size ranging from 400 micrometers to 1200 micrometers.

19. The particle of claim 1, wherein: the core contains 90% by its weight of dry crystalline choline chloride in the form of micronized crystals, the remaining 10% by weight of the core being composed of a flow modifier consisting of silica in an amount of 3% by weight of the core and by the binder acting as a moisture barrier consisting of calcium stearate in an amount of 7% by weight of the core; the core representing 44.2% by weight of the final particle; the first and second layers together representing 55.8% by weight of the final particle; the first layer is composed solely by hydrogenated soybean oil as hydrophobic substance; the second layer is composed solely by carnauba wax; the first layer represents 55% by weight of the two layers and 30.7% by weight of the final particle; the second layer represents 45% by weight of the two layers, and 25.1% by weight of the final particle; the final particle having a particle size ranging from 200 micrometers to 1000 micrometers.

20. The particle of claim 1, wherein the amount of choline chloride in the core is greater than or equal to 80% by weight of the core.

21. The particle of claim 1, wherein the amount of choline chloride in the core is equal to 85% by weight of the core.

22. The particle of claim 1, wherein the amount of choline chloride in the core ranges from 99% to 90% by weight of the core.

23. The particle of claim 1, wherein the amount of choline chloride in the core ranges from 98% to 92% by weight of the core.

24. The particle of claim 1, wherein the amount of choline chloride in the core is 93% by weight of the core.

25. The particle of claim 1, wherein the core has a weight ranging from 30% to 70% by weight of the whole particle.

26. The particle of claim 1, wherein the core has a weight ranging from 40% to 50% by weight of the whole particle.

27. The particle of claim 1, wherein the amount of carnauba wax in the second layer ranges from 80% to 100% by weight of the second layer itself.

28. The particle of claim 1, wherein the amount of carnauba wax in the second layer ranges from 90% to 95% by weight of the second layer itself.

29. The particle of claim 1, wherein the second layer further comprises a predetermined amount of a rigidity controlling agent to control the rigidity of the second layer.

30. The particle of claim 29, wherein the predetermined amount of the rigidity controlling agent is lower than or equal to 20% by weight of the second layer.

31. The particle of claim 29, wherein the predetermined amount of the rigidity controlling agent ranges from 5% to 10% by weight of the second layer.

32. The particle of claim 29, wherein the rigidity controlling agent is a plasticizer.

33. The particle of claim 29, wherein the rigidity controlling agent comprises one or more lipids.

34. The particle of claim 33 wherein the one or more lipids are selected from the family of vegetable oils.

35. The particle of claim 33 wherein the one or more lipids are selected from the group consisting of palm oil and soybean oil.

36. The particle of claim 33 wherein at least one of the one or more lipids is a hydrogenated vegetable oil.

37. The particle of claim 29, wherein the core further comprises a predetermined amount of a flow modifier.

38. The particle of claim 37, wherein the binder acts as a moisture barrier.

39. The particle of claim 37, wherein: the core contains 90% by its weight of dry crystalline choline chloride in the form of micronized crystals, the remaining 10% by weight of the core being composed of a flow modifier constituted by silica in an amount of 3% by weight of the core and by the binder acting as a moisture barrier constituted by magnesium stearate in an amount of 7% by weight of the core; the core representing 45.50% by weight of the final particle; the first and second layers together representing 54.50% by weight of the final particle; the first layer being composed solely by hydrogenated palm oil as hydrophobic substance; the second layer being composed by carnauba wax in an amount of 90% by weight of the second layer and by soybean oil as a rigidity controlling agent in an amount of 10% by weight of the second layer; the first layer representing 70% by weight of the two layers and 38.15% by weight of the final particle; the second layer representing 30% by weight of the two layers, and 16.35% by weight of the final particle; the final particle having a particle size ranging from 300 micrometers to 1200 micrometers.

40. The particle of claim 37, wherein: the core contains 85% by its weight of dry crystalline choline chloride in the form of micronized crystals, the remaining 15% by weight of the core being composed of a flow modifier comprising perlite and silica, respectively in an amount of 3% and 5% by weight of the core, and by the binder acting as a moisture barrier constituted by calcium stearate in an amount of 7% by weight of the core; the core representing 47.2% by weight of the final particle; the first and second layers together representing 52.8% by weight of the final particle; the first layer being composed solely by hydrogenated soybean oil as hydrophobic substance; the second layer being composed by carnauba wax in an amount of 90% by weight of the second layer and by palm oil as a rigidity controlling agent in an amount of 10% by weight of the second layer; the first layer representing 55% by weight of the two layers and 29.0% by weight of the final particle; the second layer representing 45% by weight of the two layers, and 23.8% by weight of the final particle; the final particle having a particle size ranging from 400 micrometers to 1200 micrometers.

41. The particle of claim 37, wherein: the core contains 85% by its weight of dry crystalline choline chloride in the form of micronized crystals, the remaining 15% by weight of the core being composed of a flow modifier comprising perlite and silica, respectively in an amount of 3% and 5% by weight of the core, and by the binder acting as a moisture barrier consisting of calcium stearate in an amount of 7% by weight of the core; the core representing 47.75% by weight of the final particle; the first and second layers together representing 52.25% by weight of the final particle; the first layer being composed solely by hydrogenated soybean oil as hydrophobic substance; the second layer being composed by carnauba wax in an amount of 95% by weight of the second layer and by palm oil in an amount of 5% by weight of the second layer; the first layer representing 50% by weight of the two layers and 26.125% by weight of the final particle; the second layer representing 50% by weight of the two layers, and 26.125% by weight of the final particle; the final particle having a particle size ranging from 400 micrometers to 1200 micrometers.

42. The particle of claim 1, wherein the second layer constitutes a percentage by weight of the two layers which ranges from 30% to 60%.

43. The particle of claim 1, wherein the second layer constitutes a percentage by weight of the two layers which ranges from 45% to 55%.

44. The particle of claim 1, wherein the first layer constitutes a percentage by weight of the two layers which ranges from 40% to 70%.

45. The particle of claim 1, wherein the first layer constitutes a percentage by weight of the two layers which ranges from 45% to 55%.

46. The particle of claim 1 wherein the hydrophobic substance is selected from the group consisting of palm oil and soybean oil.

47. The particle of claim 1, wherein the two layers constitutes a percentage by weight of the whole particle which ranges from 30% to 70%.

48. The particle of claim 1, wherein the two layers constitutes a percentage by weight of the whole particle which ranges from 50% to 60%.

49. A feed pellet containing a particle as claimed in any one of claims 1-7, 8-17, 18-37, 38, 39-45, 46 and 47-48.

50. A premix for feed containing a particle as claimed in any one of claims 1-7, 8-17, 18-37, 38, 39-45, 46 and 47-48.

51. Mash feed in unpelletted form, containing a particle as claimed in any one of claims 1-7, 8-17, 18-37, 38, 39-45, 46 and 47-48.

* * * * *